United States Patent [19]

Mosse et al.

[11] Patent Number: 4,820,717

[45] Date of Patent: Apr. 11, 1989

[54] ANTIMICROBIAL AROMATIC DERIVATIVES SUBSTITUTED BY AN (OMEGA AMINO) ALKANOL GROUP AND COMPOSITIONS CONTAINING THEM

[75] Inventors: Madeleine Mosse; Henri Demarne, both of Montpellier; Vincenzo Proietto, Saint Georges D'Orques, all of France

[73] Assignee: Sanofi, Paris, France

[21] Appl. No.: 913,361

[22] Filed: Sep. 30, 1986

[30] Foreign Application Priority Data

Oct. 11, 1985 [FR] France ............................ 85 15102

[51] Int. Cl.$^4$ ................ A61K 31/445; A61K 31/135; C07C 91/06; C07D 211/14
[52] U.S. Cl. .................... 514/317; 424/401; 424/59; 514/212; 514/307; 514/428; 514/653; 540/609; 546/149; 546/240; 548/574; 564/363; 564/364; 426/532; 426/654
[58] Field of Search ................ 546/240, 149; 424/401, 424/59; 514/212, 307, 317, 428, 653; 540/609; 548/574; 564/363, 364; 426/532, 654

[56] References Cited

U.S. PATENT DOCUMENTS 3,852,363 12/1974 Fried et al. .......................... 568/592
4,482,564 11/1984 Wright et al. ...................... 548/262

FOREIGN PATENT DOCUMENTS 642084 7/1964 Belgium .
863223 3/1961 United Kingdom .
1434826 5/1976 United Kingdom .

OTHER PUBLICATIONS

C. Metzger et al., Chemische Berichte, vol. 101(3) (1968), pp. 1120–1130.
K. Sindelar et al., Coll. Czech. Chem. Commun., vol. 46 (1981), pp. 597–606.
E. Testa et al., Jour. Org. Chem., vol. 124 (1959), pp. 1928–1936.
E. O. Bennett et al., J. Gen. Appl. Microbiol., vol. 25 (1979), pp. 63–69.

Primary Examiner—Richard L. Raymond
Attorney, Agent, or Firm—Foley & Lardner, Schwartz, Jeffery, Schwaab, Mack, Blumenthal & Evans

[57] ABSTRACT

The present invention relates to new aromatic derivatives of formula:

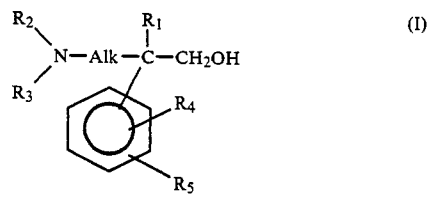

wherein:

Alk is an alkylene group with 1 to 10 carbon atoms,
$R_1$ is hydrogen or an alkyl with 1 to 6 carbon atoms,
$R_2$ and $R_3$ are similar or different and represent a cycloalkyl with 3 to 6 carbon atoms or a striaght or branched alkyl with 1 to 6 carbon atoms, either substituted or non-substituted by a phenyl or methyl phenyl group, or $R_2$ and $R_3$ form, together with the atom of nitrogen to which they are bonded, a mononitrogenous heterocycle containing no other heteroatom, such as pyrrolidino, piperidino, azepino, hexamethylene-imino, 4-methyl-piperidino, 4-phenyl-piperidino, 1,2,3,4-tetrahydro-2-isoquinolyl, 4-benzyl-piperidino;
$R_4$ is hydrogen, halogen, methyl or phenyl,
$R_5$ is hydrogen, halogen or methyl,
or $R_4$ and $R_5$ together with the benzene ring to which they are bonded, constitute a 1-naphthyl or 2-naphthyl group,
and the pharmaceutically acceptable salts with mineral or organic acids.

The invention compounds possess interesting antimicrobial properties.

12 Claims, No Drawings

ANTIMICROBIAL AROMATIC DERIVATIVES SUBSTITUTED BY AN (OMEGA AMINO) ALKANOL GROUP AND COMPOSITIONS CONTAINING THEM

The present invention relates to novel derivatives substituted by an (omega amino)alkanol group. These compounds have an antimicrobial activity.

The present invention also relates to the use of the compounds according to the invention in compositions for antiseptic or antimicrobial use, or for use as disinfectants or preserving agents, such as in the pharmaceutical, cosmetological or agri-foodstuffs industries.

Another aspect of the invention refers to the process for preparing the compounds according to the invention.

The pharmaceutical activity of certain naphtalene derivatives is known already, for example from the J. Med. Chem., 1965, 8, 589, where S. Casadio and G. Pala et al. have shown that the 1-naphthyl-1-acetonitrile display analgesic, anti-inflammatory and antispasmodic properties. And later, G. Pala et al. in J. Med. Chem. 1966, 9, 603, studied the substituted alpha derivatives of 1-naphtyl acetic acid and discovered that they had choleretic and hypoglycemia-inducing properties and no antibacterial or antifungal activity in vitro. R. K. Zahn et al. have described, in Nature, 1966 (212), 5059, 298, that the 2-naphtyl ethanol inhibits the cellular division of the lymphoma cells of mice. Finally, the 2-(6-methoxy-2-naphtyl)-2-methylethanol in its (−) form, is an anti-inflammatory known under the denomination naproxol (French Pat. No. 2,068,539 is cited as reference).

And also, phenylalkanol derivatives of formula:

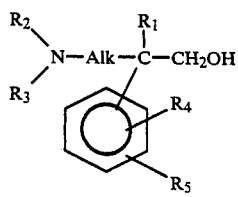

are described in Belgian Pat. No. 642,084 for their use in the treatment of nervous disorders.

It has, now, quite unexpectedly been found that the compounds (I) according to the invention, have an antimicrobial activity which is revealed by their bactericidal and fungicidal power.

The object of the present invention is to propose novel aromatic derivatives of formula:

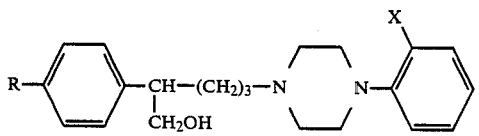

in which:

Alk is an alkylene group with 1 to 10 carbon atoms;
$R_1$ is hydrogen or an alkyl with 1 to 6 cabon atoms,
$R_2$ and $R_3$ are similar or different and represent a cycloalkyl with 3 to 6 carbon atoms or a straight or branched alkyl with 1 to 6 carbon atoms, either substituted or nonsubstituted by a phenyl or methylphenyl group;

or $R_2$ and $R_3$ form, together with the atom of nitrogen to which they are bonded, a mono-nitrogenous heterocycle containing no other heteroatom, such as pyrrolidino, piperidino, azepino, hexamethylene-imino, 4-methyl-piperidino, 4-phenyl-piperidino, 4-benzyl-piperidino, 1,2,3,4-tetrahydro-2-isoquinolyl;

$R_4$ is hydrogen, halogen, methyl or phenyl;
$R_5$ is hydrogen, halogen or methyl;
or $R_4$ and $R_5$, together with the benzene ring to which they are bonded, constitute a 1-naphthyl or 2-naphthyl group;

and the pharmaceutically acceptable salts with mineral or organic acids.

The process for preparing the compounds according to the invention consists in reducing the acid of formula:

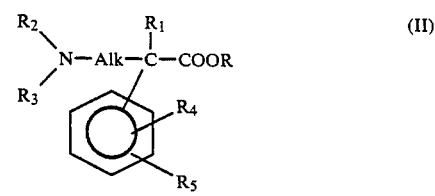

in which Alk, $R_1$, $R_2$, $R_3$, $R_4$, $R_5$ are as specified hereinabove and R is hydrogen or an alkyl group. The reduction is caused by conventional means such as by a reducing agent or an electrolysis reaction in acid medium. A suitable reducing agent is a metal hydride, used optionally in the presence of a catalyst. In particular, the reduction of the acid or ester (II) in order to obtain the compound according to the invention is caused by boron hydride, aluminium hydride; lithium, sodium or aluminium borohydride; sodium and aluminium hydride; lithium and aluminium hydride, or any other boron hydride such as borane dimethylsulphide or 1,2,3-benzodioxaborole. Preferably, the reduction is produced on the acid (R=H) or on ethyl ester (R=C₂H₅) by the action of Vitride ® (sodium bis(2-methoxy-ethoxy)aluminum hydride) in an inert solvent such as benzene or toluene at ambient temperature or at a temperature between the ambient temperature and 80° C. The resulting compound is isolated by the conventional methods, such as for example by precipitation, and thereafter eventually transformed into a pharmaceutically acceptable salt with mineral or organic acids.

The acids and their esters (II) are prepared by the conventional processes. Phenylacetonitrile substituted on the benzene ring by $R_4$ and $R_5$, or 1-naphtyl-acetonitrile, or 2-naphtyl-acetonitrile, depending on the target compound, is used as starting product and subjected to the action of sodium amide in an inert solvent brought to reflux temperature; then a chloroalkylamine of formula:

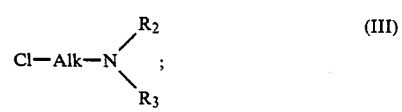

is added and the resulting mixture is heated to the solvent reflux in order to give the compound:

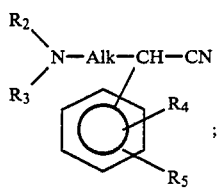

(IV)

when the substituent $R_1$ is an alkyl, the nitrile (IV) is alkylated by action of the sodium amide and of a halide $R_1X$ in order to obtain the nitrile:

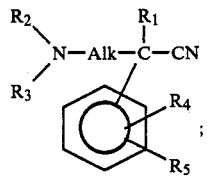

(V)

the nitrile (IV or V) is hydrolyzed in a strong acid medium (pH less than 2) in order to obtain the corresponding acid which is thereafter esterified by an alkyl group R using the conventional methods.

The bactericidal activity of the products according to the invention has been analyzed on various strains by the method described hereafter:

A bacterial inoculum is placed in contact with different dilutions of the product to be tested, and this for a limited period of time. At the end of contact, an aliquot part of the mixture bacterial suspension/product is deposited on the surface of an agar culture medium containing an agent neutralizing the antibacterial activity of the product. The bactericidal concentration retained is the smallest concentration of the product from which bacteria stop growing. Said concentration is expressed in μg/ml.

The bacterial strains selected for the analysis are:
1—*Escherichia Coli* CNCM 54125;
2—Encapsulated *klebsiella pneumoniae* R030;
3—*Pseudomonas aeruginosa* CNCM A22;
4—*Streptococcus faecalis* CNCM 5855;
5—*Staphylococcus aureus* CNCM 53154.

The second strain is supported on a Worgel Fergusson medium, the other strains being supported on Tryptic Soy Agar-Difco (TSA) commercialized by Difco.

After a 24-hour culture period at 37° C., the microbial growth is collected by means of glass beads and of 10 ml of diluent containing 1 g of tryptone and 8.5 g of sodium chloride in 1000 ml of distilled water. The formed suspension is stirred and the percentage of light transmission at 620 nm is measured with a spectrophotometer:
Strain 1: 70%
Strain 2: 80%
Strain 3: 70%
Strain 4: 60%
Strain 5: 60%

The bacterial inoculum corresponds to a 1/20th dilution of this bacterial suspension.

Plates equipped with cupules receive different dilutions of the product to be analyzed. These dilutions are placed in contact with the different bacterial suspensions by means of a multiple-center inoculator. After 20 minutes of contact, aliquot parts are transferred by means of said inoculator on the surface of an agar medium (TSA) in Petri dishes, containing an activity-neutralizing agent, namely 20 g of lubrol W, 25 g of Tween 80 and 2.5 g of sodium thiosulfate in 1000 ml of TSA (Difco). The efficiency of the neutralizing agent is controlled for each product to be analyzed by depositing on the surface of the culture medium an aliquot part of the dilution of the product to be analyzed. After drying, the corresponding inoculum is deposited in the same place. An inoculum control is performed on an agar medium with or without neutralizing agent. Readings are taken after 48 hours of incubation at 37° C.

The results are given in Table I hereunder.

TABLE I

MINIMUM BACTERICIDAL CONCENTRATION (MBC) in μg/ml

| Product No. | Bacterial strains | | | | |
| --- | --- | --- | --- | --- | --- |
| | 1 | 2 | 3 | 4 | 5 |
| SR 42 643 A | 5000 | 5000 | 1000 | 2000 | 1000 |
| SR 42 989 A | 1500 | 1500 | 1500 | 2000 | 1500 |
| SR 42 994 A | 1000 | 800 | 1000 | 1000 | 1000 |
| SR 43 063 A | 2000 | 1000 | 1000 | 2000 | 1000 |
| SR 43 077 A | 600 | 600 | 800 | 600 | 600 |
| SR 43 087 A | 1500 | 1000 | 800 | 2000 | 800 |
| SR 43 121 A | 1500 | 1500 | 1500 | 800 | 800 |
| SR 43 154 A | 2000 | 1500 | 800 | 1500 | 1000 |
| SR 43 155 A | 500 | 500 | 200 | 500 | 500 |
| SR 43 157 A | 200 | 200 | 100 | 200 | 200 |
| SR 43 245 A | 1500 | 1000 | 800 | 1500 | 1000 |
| SR 43 247 A | 300 | 300 | 300 | 300 | 500 |
| SR 43 270 A | 1000 | 1000 | 1000 | 2000 | 1000 |
| SR 43 290 A | 1500 | 800 | 800 | 4000 | 800 |
| SR 43 292 A | 300 | 300 | 300 | 300 | 300 |
| SR 43 293 A | 200 | 200 | 200 | 200 | 200 |
| SR 43 382 A | 5000 | 2000 | 2000 | 5000 | 2000 |
| SR 43 383 A | 100 | 100 | 100 | 100 | 100 |
| SR 43 703 A | 600 | 600 | 400 | 800 | 1000 |
| SR 43 705 A | 500 | 500 | 500 | 500 | 500 |
| SR 43 727 A | 20 | 50 | 50 | 20 | 200 |
| SR 43 802 A | 1000 | 1000 | 1000 | 2000 | 5000 |
| SR 43 803 A | 400 | 400 | 500 | 400 | 400 |
| SR 43 826 A | 50 | 50 | 50 | 50 | 50 |
| SR 43 940 A | 50 | 50 | 50 | 50 | 50 |
| SR 43 941 A | 50 | 50 | 50 | 50 | 50 |
| SR 43 969 A | 50 | 100 | 500 | 100 | 50 |
| SR 43 971 A | 500 | 500 | 500 | 500 | 500 |
| SR 44 027 A | 50 | 50 | 100 | 100 | 200 |
| SR 44 029 A | 10 | 50 | 50 | 50 | 50 |
| SR 44 226 A | 1000 | 1000 | 500 | 1000 | 2000 |
| SR 44 227 A | 100 | 300 | 500 | 100 | 500 |

The results show that the products according to the invention present a wide spectrum of activity on the tested bacterial strains. This bactericidal activity spreads over a short time (20 min.).

Then, for comparison, the minimum bactericidal concentration (MBC) in μg/ml of the following compounds was measured:

SR 43 970 A

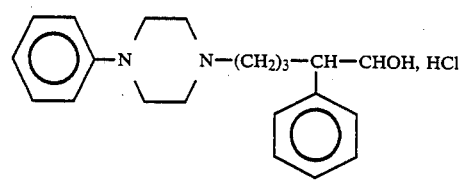

SR 43 291 A

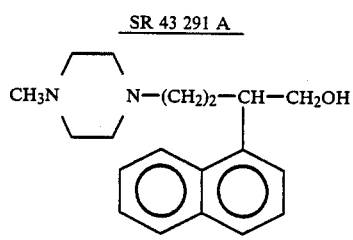

MINIMUM BACTERICIDAL CONCENTRATION
(MBC) in µg/ml

| Product No. | Bacterial strains | | | | |
|---|---|---|---|---|---|
| | 1 | 2 | 3 | 4 | 5 |
| SR 43 970 A | 5000 | 5000 | 2000 | 10000 | 5000 |
| SR 43 291A | 5000 | 3000 | 1000 | >10000 | 8000 |

Those products were found to have a bactericidal activity clearly inferior to that of the compounds according to the invention.

The antifungal activity of the products according to the invention was also determined with the aforedescribed method.

The fungal strains selected for the analysis are:
1—*Candida albicans* CNCM 1180;
2—*Candida tropicalis* 3834;
3—*Candida parakruzei* 3918;
4—*Torulopsis glabrata* 072023.

These strains are supported on a Sabouraud Dextrose agar medium commercialized by Difco; the technique used is the same as that used in the analysis of the antibacterial activity. After 48 hours of culture at 37° C., the microbial growth is collected with glass beads and 5 ml of diluent containing 1 g of tryptone and 8.5 g of sodium chloride in 1000 ml of distilled water; 5 ml of the diluent are then added. This suspension shows on the spectrometer a percentage of light transmission at 620 nm of 2 to 3%. A 1/100th dilution of this suspension, observed between slides under a microscope 40-lens, should show 10 cells per frame, this corresponding to 1,000,000 yeasts per ml.

The results are given in Table II hereunder.

TABLE II

MINIMUM FONGICIDAL CONCENTRATION
(MFC) in µg/ml

| Product No. | Yeasts strains | | | |
|---|---|---|---|---|
| | 1 | 2 | 3 | 4 |
| SR 42 994 A | 500 | 500 | 500 | 5000 |
| SR 43 077 A | 1000 | 1000 | 1000 | 5000 |
| SR 43 087 A | 1000 | 1000 | 1000 | 5000 |
| SR 43 155 A | 500 | 500 | 500 | 2000 |
| SR 43 157 A | 300 | 300 | 300 | 1000 |
| SR 43 247 A | 1000 | 500 | 1000 | 2000 |
| SR 43 270 A | 500 | 1000 | 1000 | 5000 |
| SR 43 292 A | 1000 | 1000 | 1000 | 2000 |
| SR 43 293 A | 500 | 200 | 500 | 1000 |
| SR 43 382 A | 5000 | 1000 | 2000 | 10000 |
| SR 43 383 A | 100 | 100 | 100 | 500 |
| SR 43 803 A | 1000 | 500 | 500 | 2000 |

TABLE II-continued

MINIMUM FONGICIDAL CONCENTRATION
(MFC) in µg/ml

| Product No. | Yeasts strains | | | |
|---|---|---|---|---|
| | 1 | 2 | 3 | 4 |
| SR 43 826 A | 250 | 50 | 50 | 250 |
| SR 43 941 A | 100 | 100 | 250 | 250 |
| SR 43 969 A | 50 | 50 | 100 | 500 |
| SR 44 027 A | 250 | 250 | 500 | 250 |
| SR 44 029 A | 50 | 50 | 50 | 100 |

The results show that the products according to the invention have interesting instant antifungal properties.

The tolerance of the products according to the invention was tested in the guinea-pig. The animals are shorn on both sides of the middle line of the back, the shearing being kept up every other day. Batches of 6 animals receive, on the shorn part, 0.2 ml of an aqueous or alcoholic solution of the product according to the invention. When these products are in alcoholic solution, one control batch of animals receives the alcohol on one side.

To study the preliminary skin tolerance, the treatment is applied once a day, six days out of seven, for three weeks. The observations made of the skin are concerned with the presence of erythema, skin eruptions or hyperkeratosis, the intensity of which is graduated according to a preset scale.

The skin sensitization test is performed on the same animals after two weeks' rest. The treatment lasts one week, it is identical to the preceding one. The evaluation is based on the same criteria and on the same scale as used to determine the local tolerance.

The products according to the invention have also been tested for a phototoxic or photoallergic effect on the guina-pig. The technique used is that of J. Unkovic, G. Mazue and J. Girard, in "Sciences et Techniques de l'Animal de Laboratoire", 1983, 8 (3), 149–160. This is an adaptation of the techniques described by L. C. Harber et al., Arch. Dermatol., 1967, 96, 646–656 and L. J. Vinson et al., Arch. Dermatol., 1966, 17, 123–130.

None of the products tested, namely the SR 42 643 A, SR 43 077 A, SR 43 157 A, SR 43 270 A, SR 43 292 A, SR 43 293 A, SR 43 383 A and SR 43 727 A has been found to have a bad tolerance, a sensibilizing effect, or phototoxic or photoallergic effect on the guinea-pig.

Acute toxicity was tested by oral route in mice. This test was carried out with male mice of CD1 strain, obtained from the Charles Reever breeding farm. Each batch was composed of 5 animals of body weight varying between 24 and 30 g kept in the same cage. The animals were kept fasting for 6 hours before the treatment. For every test, the product, placed in suspension in a 10% solution of gum arabic, was administered by forcible feeding with an oesophageal probe. Food was then served to the animals 4 hours after the forcible feeding and the animals were kept under observation for a period of 14 days after the administration. During that period, the death rate is recorded for each batch of animals used in the experiment and, wherever possible, the $LD_{50}$ is determined by the method of J. T. Litchfield and F. Wilcoxon, J. Pharmacol. 1949, 95, 99–113.

The results are given in mg of substance tested per kg of body weight. They are compiled in Table III below.

TABLE III

| ACUTE TOXICITY PER OS IN MICE (mg/kg) | |
| --- | --- |
| Product No. | $LD_{50}$ |
| SR 42 643 A | 400 |
| SR 42 989 A | 300–400 |
| SR 42 994 A | 750–1000 |
| SR 43 063 A | 300–400 |
| SR 43 077 A | 300–400 |
| SR 43 121 A | 300–400 |
| SR 43 155 A | below 500 |
| SR 43 292 A | 500–750 |
| SR 43 293 A | below or equal to 250 |
| SR 43 383 A | 1180 |
| SR 43 727 A | 580 |
| SR 44 027 A | 1000–1200 |

The following examples are given non-restrictively to illustrate the invention.

EXAMPLE 1

4-(N,N-diethylamino)-2-(1-naphthyl)-butanol hydrochloride

SR 42 989 A (1) 4-(N,N-diethylamino)-2-(1-naphthyl)butyronitrile 7 g of sodium amide are added in small quantities to 27.11 g of 1-naphthylacetonitrile in 210 ml of anhydrous benzene. The mixture is heated for 2 hours to reflux and 22 g of 2-chlorodiethylaminoethane are added, the heating being continued to reflux for another two and a half hours. Then, the mixture is cooled and 200 ml of water are added. After decanting, the organic phase is extracted by HCl at 10%. The aqueous phase is washed in ether, neutralized with NaOH at 10%, then extracted with ether. After evaporation of the solvents, a red oil is obtained, which is distilled in vacuo.

B.P.: 158° C.–160° C. under 0.04 mmHg i.e. 0.053 mbar;
weight: 27 g
yield: 63%.

(2) 4-(N,N-diethylamino)-2-(1-naphthyl)butyric acid ethyl ester 16 g of the previously obtained product are heated to reflux for two hours in 66 ml of an equi-volume mixture of sulphuric acid, acetic acid and water. The resulting mixture is cooled, diluted in waer and washed in ether. The aqueous phase is neutralized with soda at 30% and washed with ether. Then the aqueous phase is re-acidified with concentrated hydrochloric acid and dry-evaporated, the residue being extracted with hot ethanol. After evaporation of the ethanol, the residue is taken up with 100 ml of ethanol to which are added a few drops of concentrated sulphuric acid, and the mixture is heated for one night to reflux. After cooling, the mixture is evaporated, taken up with water, neutralized by adding sodium bicarbonate then extracted with ether, washed with water and dried over magnesium sulphate. 10 g of an orange oil are thus obtained.

Gross yield: 63.85%.

(3) SR 42 989 A 10 g of the previously obtained product are added dropwise to 15.5 g of Vitride ® (sodium bis-(2-methoxyethoxy)aluminium hydride) in solution at 70% in toluene. After two hours at ambient temperature, the mixture is poured over water and dried over magnesium sulfate. Then it is evaporated, the residue is taken up with dry ethyl ether, and hydrochloric ethyl ether is then added dropwise. The resulting mixture is again evaporated, taken up with isopropyl alcohol and anhydrous ethyl ether is added dropwise. The formed precipitate is filtered, washed with anhydrous ethyl ether and dried. 6 g of the expected product are thus obtained, which are re-crystallized in ether.

Yield=65%.
M.P.=98°–100° C.

EXAMPLE 2

8-piperidino-2-(1-naphthyl)-octanol hydrochloride

SR 43 147 A

The 1-chloro-6-piperidino hexane is prepared in the first three stages.

(1) 6-piperidino-6-oxo hexanoate of ethyl 52.2 g of adipic acid ethyl monoester are heated to reflux for one and a half hours in 30 ml of thionyl chloride, then the excess of thionyl chloride is evaporated in vacuo and the residue is taken up with 100 cm$^3$ of anhydrous ether. 58.8 g of piperidine in 100 ml of ether are added dropwise at 0° C., then the temperature is brought back to ambient temperature under stirring for one hour. The mixture is then poured over water and the organic phase is decanted, washed twice with water and then with a sodium carbonate solution at 10%, after what it is dried over magnesium sulphate and the solvent is evaporated, leaving a brown oil which is distilled in vacuo.

B.P.: 132°–136° C. under 0.025 mm of Hg, i.e. 0,033 mbar
Weight: 35 g
Yield=48%

(2) 6-piperidino-hexanol 35 g of the previously obtained product are added dropwise to 72.8 g of vitride at 70% in toluene, and the mixture is left to stand for one night at ambient temperature. It is then poured over ice, extracted with ether, washed with water, dried on magnesium sulphate and evaporated in vacuo.

24 g of colorless liquid are obtained.
Gross yield: 80%.

(3) 1-chloro-6-piperidino-hexane 16 g of thionyl chloride are added dropwise to 24 g of the previously obtained product in solution in 75 ml of chloroform. After 4 hours of heating to reflux, the solvent is evaporated, the residue is taken up with water and the solution is neutralized with soda at 10%, when the solvent is extracted with ether, washed with water, dried over magnesium sulfate and evaporated.

Weight: 22 g
Gross yield: 91.6%.

(4) 8-piperidino-2-(1-naphthyl)-octanenitrile 3.9 g of sodium amide are added in small quantities to 16.7 g of 1-naphthyl-acetonitrile in solution in 200 ml of anhydrous ether. After 2 hours of heating to reflux, 20.5 g of 6-piperidino-1-chloro-hexane are added and heating is continued to reflux for another 5 hours. Then, using the conventional methods, 30 g of product are isolated.

Yield: 89.7%.

(5) Ethyl 8-piperidino-2-(1-naphthyl)-octanoate 30 g of the previously obtained product are heated to reflux for 2 hours in 150 ml of an equi-volume mixture of sulphuric acid, acetic acid and water. After cooling, the mixture is poured over water and washed with ether, then the aqueous phase is made basic by adding soda at 30%, and the resulting oil is decanted. The organic phase is washed with ether then the oil is acidified to pH: 1 by adding concentrated hydrochloric acid, the mixture is taken up with ethanol at 100%, a few drops of concentrated sulphuric acid are added and the resulting mixture is heated for one night to reflux. The alcohol is evaporated in vacuo and the residue is taken up with water, neutralized by addition of sodium acid carbonate, extracted with ether and then washed until neutralization, and the solvent is evaporated in vacuo. 23 g of an oily product is obtained.
Yield: 67.6%.

(6) SR 43 157 A

Taking 7.5 g of the product obtained in the preceding step and using the method described in Example 1, step 3, the target product is obtained and re-crystallized in the ethanol 100-ether mixture (1/1; v/v).
Weight: 2.8 g
B.P.: 125°-129° C.
Yield: 38%

EXAMPLE 3

2-ethyl-2-(1-naphthyl)-4-piperidino-butanol hydrochloride

SR 43 245 A

(1) 2-(1-naphthyl)-4-piperidino-butyronitrile 8.2 g of sodium amide are added in small quantities on a solution of 33.4 g of 1-naphthyl acetonitrile in 450 ml of anhydrous ether. The mixture is heated for 2 hours to reflux, then 29.5 g of 2-piperidino-1-chloroethane are added, a heating to reflux is repeated for 5 hours. The mixture is then cooled, poured in water, and the organic phase is extracted 3 times with 600 ml of hydrochloric acid at 10%. The aqueous phase is washed with ether and neutralized with soda at 30%. The decanting oil is extracted, washed with sodium chloride-saturated water and dried over magnesium sulphate. After evaporation of the solvent, the resulting oil is distilled under reduced pressure (vane pump).
Weight: 41.5 g
B.P.=172°-176° C. under 0.025 mmHg i.e. 0.033 mbar.

(2) 2-ethyl-2-(1-naphthyl)-4-piperidino-butyronitrile 6.5 g of $NaNH_2$ are added in small quantities to a solution of 4.5 g of the previously obtained product with 300 ml anhydrous ether. The mixture is heated for 2 hours to reflux, and 17.44 g of ethyl bromide are added dropwise. After being heated for 5 hours under reflux, the mixture is poured on water and the organic phase is extracted with hydrochloric acid at 10%. The aqueous phase is washed with ether, and neutralized with soda at 30%. The decanting oil is extracted with ether, washed with sodium chloride-saturated water, dried on magnesium sulphate and dry-evaporated.
Weight: 44 g.

(3) 2-ethyl-2-(1-naphthyl)-4-piperidino butanamide hydrochloride

To 44 g of the previously obtained product are added 120 ml of an equi-volume mixture of water, concentrated sulphuric acid and acetic acid. After 24 hours of heating to reflux, the mixture is poured over water and neutralized with soda at 30%. The decanting oil is extracted with ether, washed with water, dried on magnesium sulphate and dry-evaporated. The residue is taken up with ether and hydrochloric acid is added dropwise. The solvent is cold-evaporated, and the product is dissolved in 200 ml of ethanol 100%, precipitated with ether, filtered, washed with ether and dried in vacuo.
Weight: 40 g.

(4) 2-ethyl-2-(1-naphthyl)-4-piperidino-butanoic acid

Gaseous hydrochloric acid is kept bubbling for one and a half hours on a solution of 20 g of the previously obtained product with 10 ml of acetic acid, the temperature being kept at below 10° C. Then 20 ml of isopentyl nitrite are added in one hour at 0° C. The mixture is heated for 7 hours at 100° C. and then left to react for 2 days at ambient temperature. The reaction product is then dried evaporated and taken up with ether, which ether is thereafter evaporated and the precipitate is dissolved in 100 ml ethanol 100; the product precipitates in ether, it is dissolved in water, neutralized with soda, washed with ether and acidified with hydrochloric acid. The product is then dry-evaporated, taken up with water, and precipitates at pH 1.3. It is then filtered, washed with cold water and dried in vacuo with phosphorous anhydride.
Weight: 10 g
Yield: 66%.

(5) SR 43 245 A 10 g of the previously obtained product added dropwise to 25 ml of vitride in 100 ml of toluene. The mixture is heated for 24 hours at 80° C., poured in water, and dried in magnesium sulphate. The resulting product is dried evaporated, taken up with ether and hydrochloric ether is added dropwise. The solvent is cold evaporated, the precipitate is dissolved in 20 of ethanol 100 and precipitated in ether; it is then filtered, washed in ether and dried in vacuo.
Weight: 2.5 g
Yield: 25%
B.P.: 162°-165° C.

EXAMPLE 4

4-(4-benzylpiperidino)-2-(3,4-dichlorophenyl)butanol hydrochloride

SR 43 696 A

(1) 4-(4-benzylpiperidino)-2-(3,4-dichlorophenyl)butyronitrile 1.95 g of sodium amide are added in small quantities to an ether solution of 9.3 g of 3,4-dichlorophenylacetonitrile. The mixture is heated for 2 hours to reflux, 11.8 g of 2-(4-benzylpiperidino)-1-chloro ethane are added and heating is repeated for another 5 hours to reflux. The resulting mixture is cooled and 200 ml of water are added, after what the organic phase is decanted, washed with water and extracted with a 10% solution of hydrochloric acid. The aqueous phase is then neutralized with soda, extracted with ether, washed with water, dried over magnesium sulfate and evaporated. 13 g of oily product are thus obtained.

Gross yield: 69%.

(2) 4-(4-benzylpiperidino)-2-(3,4-dichlorophenyl)butanoate of methyl 13 g of the product obtained in the preceding stage are heated to reflux for 2 hours in 60 ml of a sulphuric acid/water/acetic acid solution (1/1/1 in volume). The mixture is cooled, poured over water and washed in ether. The aqueous phase is washed with soda at 30%, and the oil which has formed is decanted and washed 3 times in ether. The oil is then acidified to pH 1 with hydrochloric acid at 35% and dry-evaporated. The residue is taken up with methanol containing a few drops of sulphuric acid and the mixture is heated to reflux for four hours. It is then cooled, evaporated in vacuo, taken up with water, neutralized with sodium bicarbonate, extracted by ether, washed with water, dried on magnesium sulfate then in the rotary evaporator. 9 g of the oily product are obtained.

Gross yield: 63%.

(3) SR 43 969 A 9 g of the product obtained in the preceding stage are added to 6.45 g of Vitride ® in solution in 50 ml of toluene. The mixture is stirred for 5 minutes at ambient temperature. Then it is poured over water, and the organic phase is decanted, washed with water, dried over magnesium sulfate and evaporated. The residue is taken up with ether and precipitated by addition of hydrochloric ether. The ether is evaporated, the residue is taken up with a minimum of ethanol 100 and ethyl ether is added until formation of a cloud and then crystallization. After recrystallization in an ether-ethanol mixture (1/1; v/v), 7 g of the target product are obtained.

Yield: 81.7%

B.P.: 167.5° C.

The same methods as used hereinabove were used for preparing the products according to the invention which are described in Tables IV and V hereunder. They are characterized by their melting point (M.P.) after recrystallization in a solvent. The recrystalization solvents (solvent) are used in the pure state or in equi-volume mixture. The meaning of the abbreviations is as follows:

| | |
|---|---|
| methyl alcohol | MeOH |
| ethyl alcohol | EtOH |
| isopropyl alcohol | iPrOH |
| ethyl ether | Et$_2$O |
| isopropyl ether | (iPr)$_2$O |
| dichloromethane | DCM. |

TABLE IV

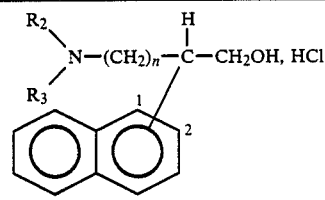

| SR No. | n | N—R$_2$R$_3$ | M.P. °C. | Solvent |
|---|---|---|---|---|
| 42 643 A | 2 | dimethylamino | 163 | EtOH/(iPr)$_2$O |
| 42 994 A | 3 | dimethylamino | 120–125 | iPrOH/Et$_2$O |
| 43 063 A | 2 | pyrrolidino | 127–132 | iPrOH/Et$_2$O |
| 43 077 A | 2 | piperidino | 168–172 | iPrOH/Et$_2$O |
| 43 087 A | 3 | piperidino | 152–155 | EtOH |
| 43 121 A | 2 | N(CH(CH$_3$)$_2$)$_2$ | 160–165 | EtOH/Et$_2$O |
| 43 154 A* | 2 | piperidino | 183–185 | EtOH |
| 43 155 A | 2 | hexamethyleneimino | 169–175 | EtOH |
| 43 247 A | 2 | 1,2,3,4-tetrahydro-2-isoquinol-yl | 173–176 | EtOH/Et$_2$O |
| 43 270 A* | 2 | hexamethyleneimino | 172–175 | EtOH/Et$_2$O |
| 43 290 A | 3 | 4-methyl-piperidino | 137–142 | EtOH |
| 43 292 A | 2 | benzyl, isopropylamino | 205–209 | MeOH/Et$_2$O |
| 43 293 A | 6 | 4-methyl-piperidino | 152–154 | MeOH/Et$_2$O |
| 43 382 A | 2 | 4-methyl-piperidino | 200–202 | EtOH/Et$_2$O |
| 43 383 A | 2 | 4-benzyl-piperidino | 185–186 | EtOH/Et$_2$O |
| 43 727 A** | 6 | dimethylamino | | RMN |
| 43 826 A** | 9 | diethylamino | | RMN |
| 43 940 A | 6 | diethylamio | 86–89 | Et$_2$O |
| 43 941 A | 5 | 4-benzyl-piperidino | 85 | DCM/Et$_2$O |
| 44 227 A | 2 | dicyclohexylamino | 110–114 | (iPr)$_2$O |

*Compounds SR 43 154 and SR 43 270 A are substituted in 2 on naphthalene. All the other compounds in this Table are substituted in 1 on naphthalene.
**Compounds SR 43 727 A and SR 43 826 A are obtained in oil form and characterized by their nuclear magnetic resonance spectrum (NMR):

SR 43 727 A (Spectrum recorded at 60 MHz)

10 protons between 0.7 and 1.9 ppm; massive; —(C$\underline{H_2}$)$_5$—CH—CH$_2$OH 8 protons between 2.3 and 3 ppm; massive; —CH$_3$)$_2$N—C$\underline{H_2}$—

3 protons between 3.4 and 3.8 ppm; massive; —C$\underline{H}$—C$\underline{H_2}$—OH 7 protons between 7.1 and 8.3 ppm; massive; aromatic H of naphthalene 1 proton at 10.4 ppm; massive; O$\underline{H}$.

SR 43 826 A (Spectrum of the product in base form, recorded at 250 MHz)

14 protons between 1 and 1.35 ppm; multiplets; (C$\underline{H_2}$)$_7$—CH$_2$—CH—CH$_2$OH;

6 protons between 0.73 and 0.96 ppm; triplets; (C$\underline{H_3}$—CH$_2$)$_2$N;

2 protons between 1.5 and 2 ppm; multiplets; —CH$_2$—CH—C$\underline{H_2}$—OH;

2 protons at 2.2 ppm; triplets; N—C$\underline{H_2}$—;

4 protons between 2.3 and 2.4 ppm; quadruplets; (CH$_3$—C$\underline{H_2}$)$_2$N;

3 protons between 3.4 and 3.7 ppm; multiplets; C$\underline{H}$—C$\underline{H_2}$—OH;

1 proton at 4.6 ppm; singulets: O$\underline{H}$;

7 protons between 7.3 and 8.2 ppm; massive; aromatic H of naphthalene.

TABLE V

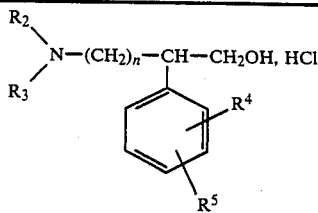

| SR No. | n | N R$_2$ R$_3$ | R$_4$, R$_5$ | M.P. °C. | Solvent |
|---|---|---|---|---|---|
| 43 110 A | 2 | piperidino | H, H | 154–158 | iPrOH/Et$_2$O |
| 43 111 A | 3 | piperidino | H, H | 120–125 | iPrOH/Et$_2$O |
| 43 120 A | 2 | pyrrolidino | H, H | 115–117 | EtOH/Et$_2$O |
| 43 408 A | 2 | piperidino | 4F, H | 165–167 | EtOH/Et$_2$O |
| 43 409 A | 2 | piperidino | 2Cl, H | 183–185 | EtOH/Et$_2$O |
| 43 703 A | 2 | hexamethyleneimino | 2Cl, 6Cl | 135–147 | EtOH/Et$_2$O |
| 43 705 A | 2 | 4-benzyl-piperidino | H, H | 170–172 | EtOH/Et$_2$O |
| 43 802 A | 2 | hexamethyleneimino | 2Cl, 4Cl | 162–165 | iPrOH/Et$_2$O |
| 43 803 A | 2 | hexamethyleneimino | 3Cl, 4Cl | 155 | iPr OH |
| 43 971 A | 2 | 4-benzyl piperidino | 3Cl, 4Cl | 176–179 | EtOH/Et$_2$O |
| 44 027 A | 2 | 4-benzyl piperidino | 2Cl, 4Cl | 160–162 | EtOH/Et$_2$O |
| 44 028 A | 2 | 4-benzyl piperidino | 2Cl, 6Cl | 160–162 | EtOH/Et$_2$O |
| 44 029 A | 2 | 4-benzyl piperidino | 4C$_6$H$_5$, H | 211–213 | EtOH/Et$_2$O |
| 44 226 A | 2 | 4-benzyl piperidino | 3CH$_3$, H | 172–175 | EtOH/Et$_2$O |
| 44 245 A** | 6 | diethylamino | 3Cl, 4Cl | | RMN |
| 44 246 A | 2 | 4-benzyl-piperidino | 2Cl, H | 178–180 | iPrOH |

Compound SR 44 245 A obtained in oil form is characterized by its NMR spectrum recorded at 250 MHz.

SR 44 245 A 16 protons between 0.96 and 1.72 ppm; massive; N(CH$_2$CH$_3$)$_2$, (CH$_2$)$_4$ and

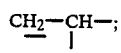

1 proton between 2.55 and 2.70 ppm; massive;

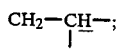

6 protons between 2.8 and 3.10 ppm; massive; N—(CH$_2$CH$_3$)$_2$ and

2 protons between 3.4 and 3.5 ppm; massive; CH$_2$OH;
1 proton between 4.6 and 4.7 ppm; triplets; OH;
1 proton between 7.12 and 7.19 ppm; doublets: aromatic H;
1 proton at 7.4 ppm; singulets; aromatic H;
1 proton betwen 7.45 and 7.50 ppm; doublets; aromatic H.

Different galenic formulations of the products according to the invention can be prepared depending on the target application.

EXAMPLE 5

| Alcoholic antiseptic solution | |
|---|---|
| SR 43 383 A | 0.2 g |
| Alkyldimethylcarboxymethylamine (in solution at 30%) | 15 g |
| Disodic tetracemate | 0.1 g |
| Propylene glycol | 20 g |
| Sodium hydroxide s.q.f. pH 5.8 | |
| Purified water s.q.f. | 100 g |

EXAMPLE 6

| Foaming detergent liquid antiseptic preparation | |
|---|---|
| SR 43 293 A | 0.5 g |
| Sodium sulphonate paraffin | 15 g |
| Sodium hydroxyde or lactic acid s.q.f. pH 5.2 | |
| Purified water s.q.f. | 100 g |

EXAMPLE 7

| Antiseptic alcoholic solution | |
|---|---|
| SR 43 247 A | 0.5 g |
| Alkyldimethylcarboxymethylamine (solution at 30%) | 0.5 g |
| Condensate of ethylene oxide and of propylene glycol L 62 | 1 g |
| Lactic acid or sodium hydroxide s.q.f. pH 6.5 | |
| Ethyl alcohol at 70° s.q.f. | 100 g |

EXAMPLE 8

A product according to the invention can be used as preservative in a shampoo.

| Potassium palmitate and amino acids | 20 g |
|---|---|
| Sodium alkylsulphates | 2 g |
| Coprah diethanolamide | 5 g |
| Linalyle acetate | 0.200 g |
| SR 43 157 A | 0.100 g |
| Sodium hydroxide s.q.f. pH 7 | |

| -continued | |
|---|---|
| Purified water s.q.f. | 100 g |

EXAMPLE 9

A product according to the invention can be used as a preservative in an emulsion cream.

| Vaseline oil | 6 g |
|---|---|
| Mixture of cetostearyl alcohol and of oxyethylene cetostearyl alcohol | 9 g |
| Anhydrous monosodic phosphate | 0.300 g |
| Disodic tetracemate | 0.010 g |
| Vaseline | 15 g |
| SR 43 292 A | 0.100 g |
| Phosphorous acid s.q.f. pH 4.5 | |
| Purified water s.q.f. | 100 g |

EXAMPLE 10

The product according to the invention can be used as a preservative in a cream for cosmetological use.

| Collagen | 0.500 g |
|---|---|
| Carboxypolymethylene 934 | 0.400 g |
| Hydrogenated lanolin | 4 g |
| Perhydrosqualene | 20 g |
| Polyoxyethylene sorbitol monopalmitate | 2 g |
| SR 43 293 A | 0.150 g |
| Lactic acid or sodium hydroxide s.q.f. pH 6.5 | |
| Purified water s.q.f. | 100 g |

EXAMPLE 11

| Preservative in a cream for cosmetological use | |
|---|---|
| Collagen | 0.500 g |
| Carboxypolymethylene 934 | 0.400 g |
| Hydrogenated lanolin | 4 g |
| Perhydrosqualene | 20 g |
| Polyoxyethylene sorbitol monopalmitate | 2 g |
| SR 43 940 A | 0.150 g |
| Lactic acid or sodium hydroxide s.q.f. pH 6.5 | |
| Purified water s.q.f. | 100 g |

EXAMPLE 12

| Preservative in a sun-protection oil | |
|---|---|
| Mineral oil 65/75 | 68 g |
| Castor oil | 8 g |
| Sesame oil | 20 g |
| Isopropyl alcohol | 2 g |
| Eusolex 6300 | 1.5 g |
| Perfume | 0.4 g |
| SR 43 292 A | 0.100 g |

EXAMPLE 13

| Preservative in a sun-protection oil | |
|---|---|
| Mineral oil 65/75 | 68 g |
| Castor oil | 8 g |
| Sesame oil | 20 g |
| Isopropyl alcohol | 2 g |
| Eusolex 6300 | 1.5 g |
| Perfume | 0.4 g |

| -continued | |
|---|---|
| Preservative in a sun-protection oil | |
| SR 44 029 A | 0.100 g |

EXAMPLE 14

| Preservative for fruit juices or jams | |
|---|---|
| Micronized SR 43 383 A | 0.02% |

EXAMPLE 15

| Disinfectants for inert surfaces | |
|---|---|
| SR 43 157 A | 2 g |
| Dodecyldimethylcarboxydimethylamine | 20 g |
| Disodic tetracemate | 2 g |
| Lactic acid s.q.f. pH 3.5 | |
| Purified water s.q.f. | 100 g |

EXAMPLE 16

| Disinfectants for inert surfaces | |
|---|---|
| SR 44 027 A | 2 g |
| Dodecyldimethylcarboxydimethylamine | 20 g |
| Disodic tetracemate | 2 g |
| Lactic acid s.q.f. pH 3.5 | |
| Purified water s.q.f. | 100 g |

EXAMPLE 17

Protection of the viscosity-inducing agents used in improved recovery of hydrocarbons:

Aqueous solution at 1000 ppm of synthetic polymer (polyacrylamide) or biopolymer (xanthane)

SR 43 727 A: 1000 ppm.

Such a biocide concentration protects the aqueous solution of polymer or of biopolymer from biodegradation in the reservoir during the hydrocarbons recovery phase.

We claim:

1. A compound corresponding to the formula:

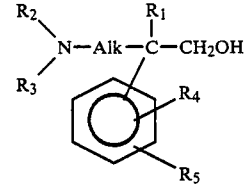

wherein:

Alk represents an alkylene group with 2 to 10 carbon atoms, $R_1$ represents hydrogen or an alkyl group with 1 or 2 carbon atoms, $R_2$ represents a cyclohexyl group or a straight or branched alkyl group with 1 to 3 carbon atoms, $R_3$ represents a cyclohexyl group, a straight or branched alkyl group with 1 to 3 carbon atoms, or benzyl, or $R_2$ and $R_3$ together with the nitrogen atom to which they are bonded to form a heterocycle selected from the group consisting of pyrrolidino, piperidino, azepino, hexamethyleneimino, 4-methylpiperidino, 4-phenylpiperidino, 4-benzylpiperidino, or 1,2,3,4-tetrahydro-2-isoquinolyl, R₄ represents hydrogen, halogen, methyl or phenyl,
R₅ represents hydrogen, halogen or methyl, or
R₄ and R₅ together with the benzene ring to which they are bonded constitute 1-naphthyl or 2-naphthyl, or a pharmaceutically acceptable salt with a mineral or organic acid thereof.

2. A compound according to claim 1, which is 4-(4-benzylpiperidino)-2-(1-naphthyl)butanol or a pharmaceutically acceptable salt with a mineral or organic acid thereof.

3. A compound according to claim 1, which is 8-(N,N-dimethylamino)-2-(1-naphthyl)octanol or a pharmaceutically acceptable salt with a mineral or organic acid thereof.

4. A compound according to claim 1, which is 8-(N,N-diethylamino)-2-(1-naphthyl)octanol or a pharmaceutically acceptable salt with a mineral or organic acid thereof.

5. A compound according to claim 1, which is 4-(4-benzylpiperidino)-2-(2,4-dichlorophenyl)butanol or a pharmaceutically acceptable salt with a mineral or organic acid thereof.

6. A compound according to claim 1, which is 4-(4-benzylpiperidino)-2-(4-phenylphenyl)butanol or a pharmaceutically acceptable salt with a mineral or organic acid thereof.

7. An antimicrobial liquid composition comprising a liquid selected from the group consisting of water and lower alkyl alcohols and an effective antimicrobial amount of a compound corresponding to the formula:

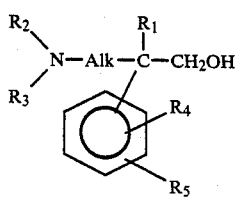

wherein:
Alk represents an alkylene group with 2 to 10 carbon atoms,
R₁ represents hydrogen or an alkyl group with 1 or 2 carbon atoms,
R₂ represents a cyclohexyl group or a straight or branched alkyl group with 1 to 3 carbon atoms,
R₃ represents a cyclohexyl group, a straight or branched alkyl group with 1 to 3 carbon atoms, or benzyl, or
R₂ and R₃ together with the nitrogen atom to which they are bonded form a heterocycle selected from the group consisting of pyrrolidino, piperidino, azepino, hexamethyleneimino, 4-methylpiperidino, 4-phenylpiperidino, 4-benzylpiperidino, or 1,2,3,4-tetrahydro-2-isoquinolyl,
R₄ represents hydrogen, halogen, methyl or phenyl,
R₅ represents hydrogen, halogen or methyl, or
R₄ and R₅ together with the benzene ring to which they are bonded constitute 1-naphthyl or 2-naphthyl, or a pharmaceutically acceptable salt with a mineral or organic acid thereof.

8. A composition according to claim 7, wherein said compound is 4-(4-benzylpiperidino)-2-(1-naphthyl)-butanol or a pharmaceutically acceptable salt with a mineral or organic acid thereof.

9. A composition according to claim 7, wherein said compound is 8-(N,N-dimethylamino)-2-(1-naphthyl)octanol or a pharmaceutically acceptable salt with a mineral organic acid thereof.

10. A composition according to claim 7, wherein said compound is 8-(N,N-dimethylamino)-2-(1-naphthyl)octanol or a pharmaceutically acceptable salt with a mineral or organic acid thereof.

11. A composition according to claim 7, wherein said compound is 4-(4-benzylpiperidino)-2-(2,4-dichlorophenyl)-butanol or a pharmaceutically acceptable salt with a mineral organic acid thereof.

12. A composition according to claim 7, wherein said compound is 4-(4-benzylpiperidino)-2-(4-phenylphenyl)butanol or a pharmaceutically acceptable salt with a mineral or organic acid thereof.

* * * * *